United States Patent [19]
Trinidad

[11] Patent Number: 6,086,822
[45] Date of Patent: Jul. 11, 2000

[54] METHODS AND APPARATUS FOR STEAM STERILIZATION WITH REDUCED WATER CONSUMPTION

[76] Inventor: Michael A. Trinidad, 9 Columbia Ave., Natick, Mass. 01760

[21] Appl. No.: 09/033,137

[22] Filed: Mar. 2, 1998

Related U.S. Application Data

[60] Provisional application No. 60/040,010, Mar. 3, 1997.
[51] Int. Cl.$^7$ ...................................................... A61L 2/08
[52] U.S. Cl. ............................ 422/26; 422/108; 422/109; 422/110; 422/295
[58] Field of Search .............................. 422/26, 295, 297, 422/292, 108–110

[56] References Cited

U.S. PATENT DOCUMENTS

| | | | |
|---|---|---|---|
| 4,944,919 | 7/1990 | Powell | 422/26 |
| 5,026,524 | 6/1991 | Powell et al. | 422/26 |

*Primary Examiner*—Krisanne Thornton

[57] ABSTRACT

The invention provides improved methods and apparatus for steam sterilization that monitor pressure at one of more points in the steam flow path in order to regulate the flow of cooling water mixed into the discharge or effluent. This permits the indirect, yet accurate and rapid, determination of discharge water temperature so that it can be mixed with just the right amount of cooling water to bring it to the desired temperature, e.g., 140° F. or below.

3 Claims, 2 Drawing Sheets

METHODS AND APPARATUS FOR STEAM STERILIZATION WITH REDUCED WATER CONSUMPTION

BACKGROUND

This application claims the benefit of United States Provisional Patent Application Ser. No. 60/040,010, filed Mar. 3, 1997.

This invention relates to steam sterilizers and, particularly, to methods and apparatus for steam sterilization with reduced water consumption.

Steam sterilization is used in hospitals, labs and other similar businesses as the last step in cleaning biological contaminates from instruments so they can be reused in future procedures. Specially built cabinets are designed and certified to perform this function. Typically, instruments are washed, dried and wrapped in a cloth. The wrapped instruments are then placed in a sterilization cabinet.

There are several ways to sterilize instruments. The standard sterilization process consists of four steps. During the first step, the inner chamber is prepared by the introduction of steam to purge the air from the chamber and to heat the instruments within it. Next, this chamber is filled and held with steam for 5 to 10 minutes. This is the sterilization step, which kills any organisms on the instruments by exposing them to high temperatures. Next, a vacuum is drawn to reduce the pressure in the chamber (e.g., to 18–24 inches Hg) and, thereby, to dry the instruments.

An outer chamber (or jacket) of the sterilizer furnishes radiant heat and aids in drying instruments contained in the inner chamber. A steel shell, which separates this jacket from the inner chamber, allows the heat from the jacket to radiate to the inner chamber. The drying process can last from 10 to 25 minutes.

The final step introduces air back into the inner chamber through an air valve and returns it to atmospheric pressure. As designed by most manufacturers, a constant flow of steam is provided to the jacket in order to keep it hot both during and between sterilization batches.

Any time a conventional sterilizer is turned on, it will be heated by steam in either the jacket or the inner chamber or both. The end result of heating with steam is hot condensate. Condensate is nothing more than hot liquid water. It is a property of water that occurs when steam gives up its heat to a cold surface. The temperature of this liquid is about 240° F. As the liquid leaves the sterilizer, it gets mixed with city water to cool it to within 140° F. Building codes require this discharge water temperature to be at or below 140° F.

An object of this invention is to provide improved methods and apparatus for steam sterilization and, more particularly, to provide such methods and apparatus as reduce the amount of water consumed thereby.

Another object of this invention is to provide such methods and apparatus as provide better control of the water temperature than conventional sterilizer systems.

Yet another object of the invention is to provide such methods and apparatus as permit water usage to be controlled better than conventional sterilizer systems.

SUMMARY

The invention achieves these and other objectives by providing improved methods and apparatus for steam sterilization that monitor pressure at one of more points in the steam flow path in order to regulate the flow of cooling water mixed into the discharge or effluent. This permits the indirect, yet accurate and rapid, determination of discharge water temperature so that it can be mixed with just the right amount of cooling water to bring it to the desired temperature, e.g., 140° F. or below.

Unlike prior art sterilizers, that do not selectively regulate cooling water flow, or that do so via the use of temperature sensors, the monitoring of pressure affords higher savings than temperature controls, which react more slowly. Moreover, it eliminates the possibility of temperature sensor failure due to inaccurate placement within the sterilizers discharge pipe.

Systems according to the invention are also beneficial since they can be retrofit to existing steam sterilizers without adversely impacting any of the existing manufacturer's controls.

BRIEF DESCRIPTION OF THE DRAWINGS

A more complete understanding of the invention may be attained by reference to the drawings in which.

DETAILED DESCRIPTION OF THE ILLUSTRATED EMBODIMENT

Figure 1:
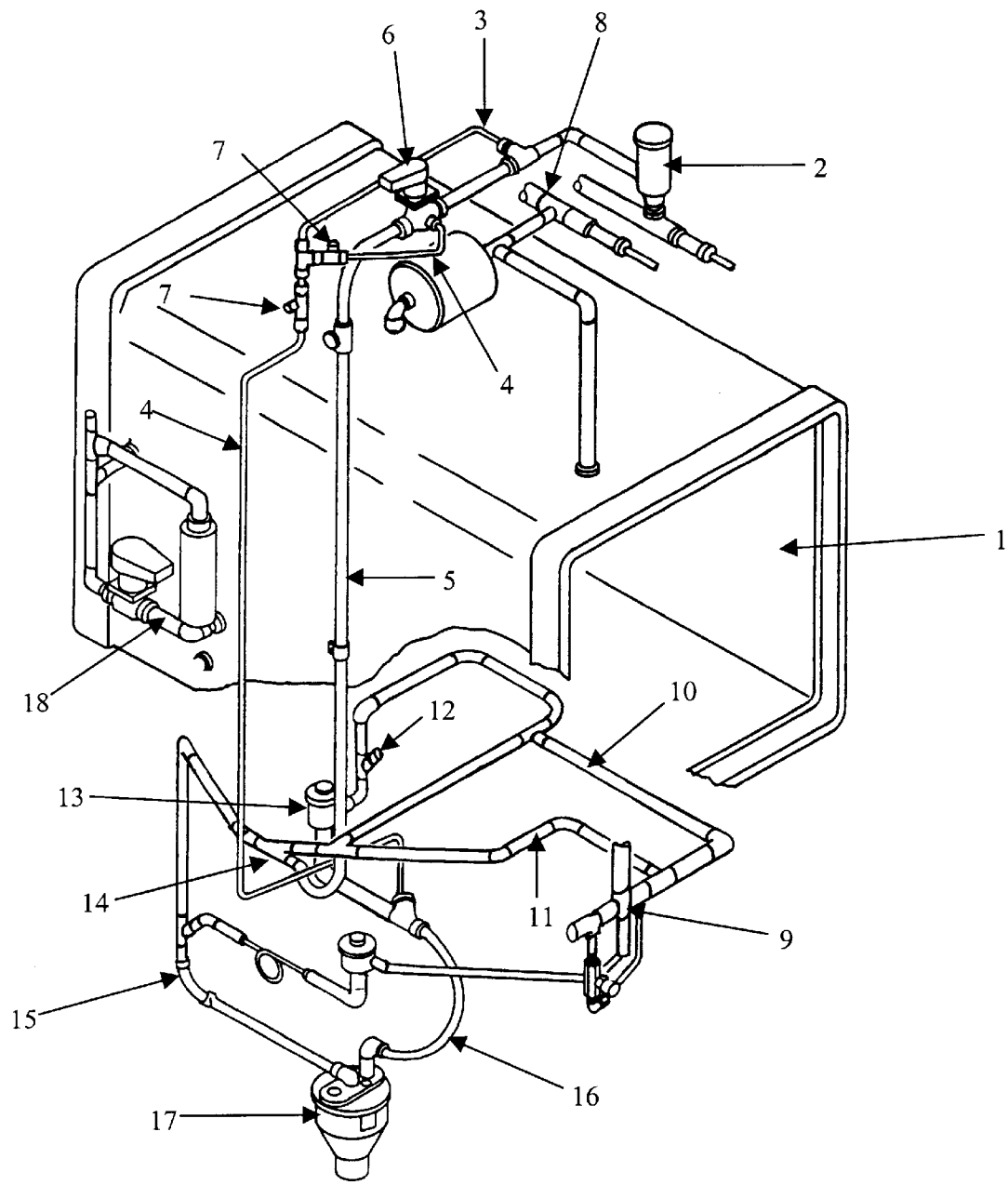
FIG. 1 illustrates a prior art steam sterilizer.

FIG. 1 shows the major components of a conventional steam sterilizer. These components are inner chamber 1, water piping 2–5, main water control valve 6, needle valves 7, main steam valve 8, inner chamber drain piping 9–11, jacket drain piping 12, jacket steam trap 13, condensing pipe 14, drain piping 15 and 16, drain funnel 17 and air valve 18.

As described earlier, when the main water control valve 6 is closed water continues to by pass it through the by pass line 3. This occurs by the manufacturer's design. The water is then regulated by the needle valves 7. These valves are adjusted to maintain a flow rate of one to two gallons per minute. The water then passes into the bleed lines 4. Finally, it makes its way into the piping 5, 14, 15 and 16, where it is intended to mix with the hot steam and condensate and cool it to within 140° F. There are two paths within the sterilizer that the steam takes. One is through the inner chamber 1. The other path is through the jacket. Both paths produce hot condensate and therefore require the need for city water to cool it down.

Most sterilizers operate on a four step sterilization process. The instruments to be sterilized have been previous washed, covered in a cloth and placed in the sterilizer's inner chamber. The door is locked and air is removed through one or more purging processes. During a purge, an air valve 18 and steam valve 8 are open causing air to be pushed out of the inner chamber by the steam. Both before and during the purging process water is by-passing around a closed water valve 6. During these conditions water is being needlessly wasted.

Once the purge process has occurred the chamber is pressurized and held at 20 to 30 psig for several minutes. The hot steam comes in contact with the relatively cooler instruments and in the process of transferring its heat returns it back from a vapor to a liquid. It is important that the instruments remain dry during and after the sterilization process. Each manufacturer has their own methods for removing the condensate during the sterilization step. It's removed without loss of pressure to the chamber. This is accomplished by periodically opening the steam valve 8 with each discharge of condensate. This cycle of admitting steam and removing condensate continues constantly during this step. The main water valve 6 has been closed during this phase but the by-pass line is continuously feeding water around the main water valve and into the drain. In this step, it cools the condensate from the inner chamber.

Once the sterilization step is complete a drying step may occur. The main water valve 6 opens along with a chamber drain valve 9. The pressure continuously drops. Some steam sterilizers are specially designed to develop a vacuum. The vacuum produces a high negative pressure which assists in vaporizing (drying) water that has worked its way into the cloth covered instruments. The main water valve remains open. The water is used to cool the condensate and (in some models) pull a vacuum using a venturi. The bleed lines are still by-passing water around the open water valve. In this step, the bleed lines are needlessly wasting water.

The last step returns the chamber to atmospheric pressure allowing the instruments to be removed from the inner chamber. The bleed lines will continue to by-pass water around the closed water valve. In this step and between sterilizations the bleed lines are needlessly wasting water.

The jacket operates independently of the sterilization process. When the sterilizer is turned on the jacket is supplied with steam. The jacket remains hot until a manual steam valve is shut off by an operator. This, in practice, never occurs. Therefore, even when the sterilizer is not being used the jacket is heated by steam. The steam eventually gives up its heat to the walls of the jacket and returns to a liquid state. A steam trap 13, located below the jacket begins to collect this liquid within it. As the liquid accumulates it cools below the 240° F. steam temperature. The steam trap 13 has a sensing element, which measures this decrease in temperature and causes the trap to open and release the condensate into the drain line 16. As the condensate leaves, steam will quickly follow and will heat the element back up causing the trap to seal off the jacket from the drain piping. This will occur until condensation begins to collect in the trap again.

The problem with the operation of prior art steam sterilizers are their wasteful use of cooling water. There are times when there is no steam or condensate to be cooled, yet the cooling water continues to flow. In some cities this can amount to over $8,000 dollars per machine per year in needless operating costs.

Figure 2:
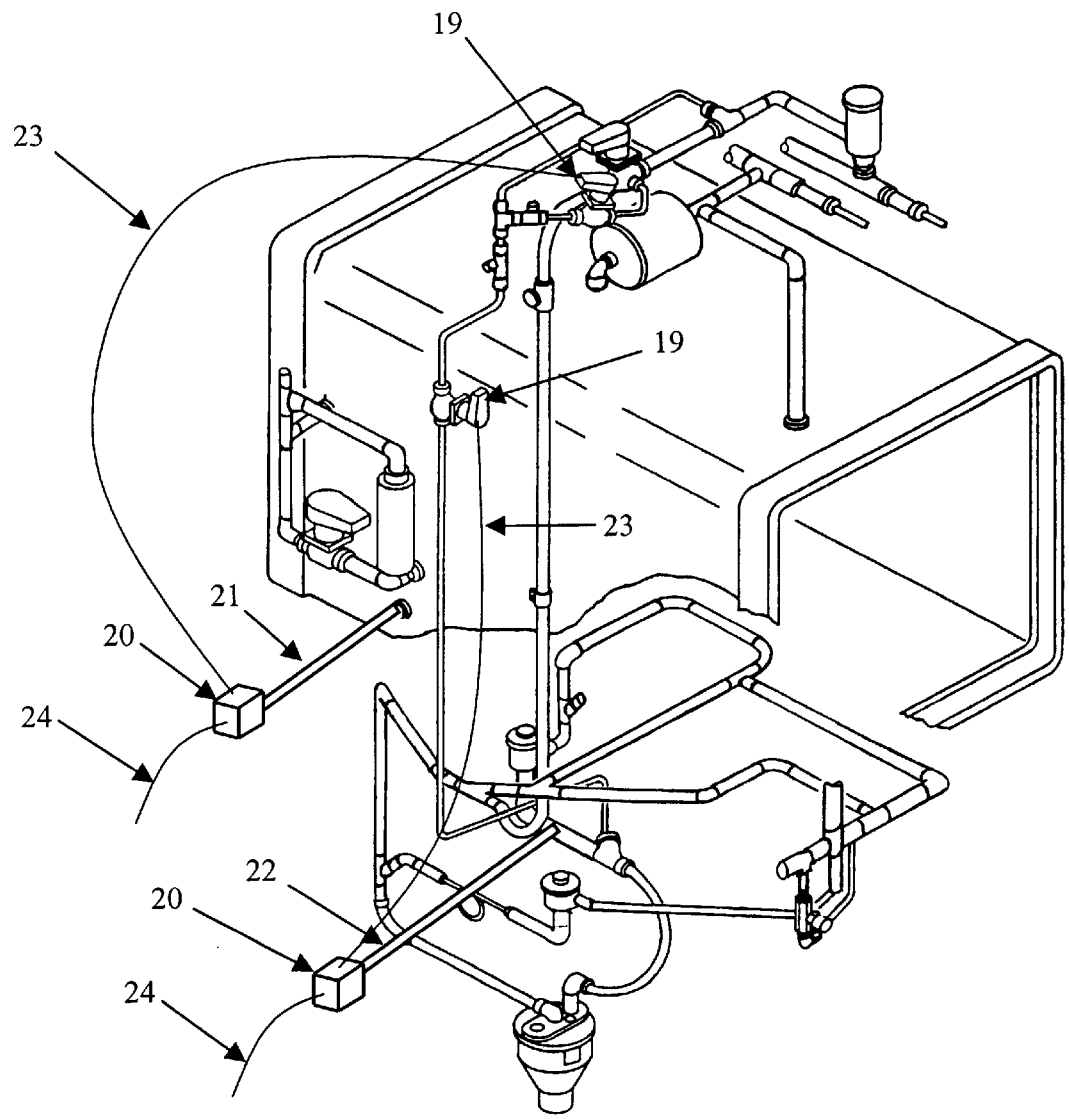
FIG. 2 depicts a steam sterilizer according to the invention.

FIG. 2 shows a steam sterilizer according to the invention. Though the illustrated embodiment is constructed by retrofitting several new components onto a prior art sterilizer of the type shown in FIG. 1, those skilled in the art will appreciate that systems according to the invention can be fabricated from scratch or by retrofitting prior art systems of entirely different design.

Referring to FIG. 2, several new components that have been added to the sterilizer in FIG. 1. These components are: solenoid valves 19, pressure sensors 20, pressure sensing piping 21 and 22, control wiring 23 and power wiring 24. For maintenance and safety reasons, a preferred embodiment utilizes a shut off valve in the pressure sensing lines 21 and 22 and an electrical disconnect switch between the power source and the pressure switches 20.

The underlying principle behind this invention comes from the realization that cooling water consumption can be effectively reduced by monitoring pressure at various points in the steam flow path.

There are two conditions that require cooling water. The first is when the inner chamber is filled with steam (usually 20 to 30 psig). The second is when the jacket steam trap 13 opens. Both of these conditions will release hot condensate into the drain lines 14, 15, 16, and 17. The existing sterilizers address this by supplying a separate water line designed to mix a continuous stream of water with the hot condensate.

The illustrated sterilizer takes two pressure readings: one in the inner chamber 21, the other in the drain line connected to the jacket trap 22. When the inner chamber is empty or under a vacuum (drying)—i.e., as reflected by an inner chamber pressure at or below zero gage pressure (0 psig)—there is no need for cooling water.

Likewise, when the jacket trap is closed and the drain piping is open only to the atmosphere—i.e., as reflected by zero gage pressure (0 psig) in the drain line downstream from the trap 22—there is no need for cooling water. This latter condition can be best appreciated by understanding that when the jacket trap 22 opens, the 60 psig of steam pushes the accumulated hot condensate through the trap and into the drain piping. The result is the piping being pressurized above atmospheric pressure.

With particular reference to FIG. 2, the illustrated components cooperate to regulate cooling water flow as follows. The steam trap 13 and inner chamber 1 have different needs and therefore have independent control systems. The action of one has no effect on the other. The inner chamber system will be described first followed by a discussion of the steam trap system.

During the start of the sterilization process the air valve 18 is open and the inner chamber 1 is filled with steam. The inner chamber 1 will remain near atmospheric pressure and the pressure sensing tube 21 will see less than 5 psig in the inner chamber 1. The pressure switch 20 will be closed causing 120 volts to be sent to the solenoid valve 19. The 120 volts will energize the solenoid valve 19 and cause it to close off the flow of water.

After a brief purge, the air valve 18 will close causing the inner chamber pressure to quickly rise and initiate the sterilization step. The sensing tube 21 will relay that sudden increase in pressure to the pressure switch 20 causing it to open the electric circuit and deenergize the solenoid valve 19. The de-energized solenoid valve will open the flow of water in the associated bleed line 4 causing it to instantly mix with the steam and hot condensate from the drainage tubing 9, 10 and 11 at the condensing fitting 14. The combined water temperature will be at 140° F. or below when it passes into the drain funnel 17.

Next a vacuum will be drawn causing the inner chamber pressure to drop. All the steam and condensate will be evacuated and the main water valve 6 will open. During this drying phase the inner chamber 1 will be below atmospheric pressure. The sensing tube will relay that pressure to the pressure switch 20 causing the switch to close and energizing the solenoid valve 19. The energized solenoid valve will close causing the water through the bleed line 4 to stop. The remainder of the hot steam and condensate will be cooled by the main water valve 6 during the drying process.

After drying the air valve 18 will open causing the chamber to return to atmospheric pressure. The bleed line 4 will remain closed until the start of the next sterile cycle, failure of the solenoid valve or a loss of electrical power. This combination of switching and valves allows the sterilizer to return to its original operation should any of the invention's components fail. This design is intentional so that the sterilizer will never pass hot condensate to the drain and be in violation of building codes.

As stated earlier, the steam trap 13 removes the hot condensate from the jacket by knowing when condensate is present and then opening a passage within it to allow it to exit down the drain line 16 and into the drain funnel 17. The act of opening the jacket (60 psig) to the drain line (initially at 0 psig) causes an instant increase in pressure (about 30 psig). This increase in pressure is transmitted through the sensing piping 22 to the pressure switch 20. The action of the pressure switch and the associated solenoid valve are the same as the inner chamber system. The also provide the same fail-safe design. Prior art has tried measuring the temperature of the steam trap effluent and controlling the associated control valve with little success. The trap may only open for 1 to 2 seconds. By the time the temperature sensor has figured out that its hot the steam and condensate have already passed into the drain. In addition the mass of the sensor retains the heat and causes the solenoid valve to remain open much longer than what is needed. The combined effect of a temperature based control is code violations and excessive water usage.

Unlike systems that utilize temperature sensors, the use of pressure sensors insures that there is no delay between the time the chamber or the drain piping is pressurized and the delivery of the cooling water. The steam and hot condensate are instantly cooled to 140° F. Thus, for example, when the trap 22 closes, the downstream drain piping returns to atmospheric pressure and the water line shuts down.

Components 19 to 24 comprise conventional equipment of their respective types commercially available in the marketplace. Pressure switches 20 are preferably 120 V, single phase and be able to be wired normally closed. They are also preferably adjusted to operate on a signal of 5 psig or greater. The solenoid valves 19 are preferably 120 V, single phase, normally open with a CV=2.0. The pressure sensing tube 21 and 22 is preferably ¼" refrigeration copper tubing supplied with a ¼" shut-off valve rated for steam service. The control and power wiring 23 and 24 are preferably 14 gage, 3 wire, shielded cable, each pressure switch shall have its own disconnect switch. The power for the control is preferably taken off of the main electric feed to the sterilizer. The connection is preferably made upstream of the units inline electronic filtering system.

Needle valves are preferably adjusted to produce 140° F. (or less) in the drain funnel 17 when the pressure switches 20 cause the solenoids to open 19, allowing the water to mix with the hot condensate. Of course, those skilled in the art will appreciate that quantities expressed in this paragraph are merely by way of example and that other embodiments may utilize elements of differing capacity in their stead.

Described above are methods and apparatus for steam sterilization meeting the objects set forth. Those skilled in the art will appreciate that the illustrated embodiment is but one example of the invention, which may be embodied in systems incorporating modifications thereto. In view of the foregoing, what I claim is:

1. A method of reducing water consumption in a steam sterilizer comprising:

disposing at least one pressure sensing device in any of a steam supply path and an effluent discharge path;

operationally coupling a fluid flow regulator to a coolant supply and the at least one pressure sensing device;

monitoring pressure at the at least one pressure sensing device;

regulating flow of coolant from the coolant supply through any of a steam supply path and an effluent discharge path upon the occurrence of a predetermined pressure threshold as sensed by the at least one pressure sensing device.

2. The method of claim 1 wherein coolant flow is activated when the at least one pressure sensing device detects a pressure in excess of the predetermined pressure.

3. The method of claim 2 wherein the predetermined pressure is at or about 5 psig.

\* \* \* \* \*